(12) United States Patent
Faccioli et al.

(10) Patent No.: US 6,235,029 B1
(45) Date of Patent: *May 22, 2001

(54) ORTHOPAEDIC DEVICE FOR THE GRADUAL CORRECTION OF LIMBS

(75) Inventors: Giovanni Faccioli, Monzambano; Daniele Venturini, Povegliano Veronese; Sander Ten Veldhuijs, Verona, all of (IT)

(73) Assignee: Orthofix S.R.L., Bussolengo Verona (IT)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/022,153

(22) Filed: Feb. 11, 1998

(30) Foreign Application Priority Data

Feb. 14, 1997 (IT) .............................. VR97A0013

(51) Int. Cl.⁷ .................................................. A61B 17/64
(52) U.S. Cl. .................................. 606/54; 606/57; 606/59
(58) Field of Search ................................ 606/54, 55, 56, 606/57, 58, 59

(56) References Cited

U.S. PATENT DOCUMENTS

| 2,391,537 | * | 12/1945 | Anderson | ............................... 606/59 |
| 4,502,473 | | 3/1985 | Harris et al. | |

(List continued on next page.)

FOREIGN PATENT DOCUMENTS

| 0385929 | 9/1990 | (EP) . |
| 0699419 | 3/1996 | (EP) . |
| 2557933 | 1/1984 | (FR) .................................. F16B/9/02 |
| 2645428 | 10/1990 | (FR) . |
| 9111151 | 8/1991 | (WO) ............................. A61B/17/60 |
| 9202184 | 2/1992 | (WO) . |

OTHER PUBLICATIONS

Pfeil, "Heidelberg External Fixation, Unilateral Fixation Techniques in Limb Deformity Corrections," George Thieme Verlag, 1998 Wandrey trans. (1st ed. 1994), 48 pages.

Orthofix Srl., "Orthofix® Modulsystem," General Application Instructions, Jan. 1996, 28 pages.

Orthofix Srl., "Orthofix® Modulsystem", Jul. 1997, prior edition before Feb. 11, 1997, 16 pages.

Saleh, "Orthofix® Modulsystem, Operative Technique, Limb Reconstruction System", Orthofix Srl., Mar. 1998, prior edition before Feb. 11, 1997, 67 pages.

Eurpean Search Report, Application Number EP 97 12 2922, Mar. 17, 1999, 2 pages.

Primary Examiner—Michael Buiz
Assistant Examiner—David O. Reip
(74) Attorney, Agent, or Firm—Hopgood, Calimafde, Kalil & Judlowe, LLP

(57) ABSTRACT

An orthopaedic device for the gradual correction of angular and longitudinal defects of elongated bones, comprising at least one first clamp for a first group of screws insertable in a proximal portion of a bone, and at least one second clamp for a second group of screws insertable in a distal portion of the bone, a longitudinal guide bar positioned externally of the limb to be corrected for slidably supporting the clamps; at least one of the clamps is selectively orientable about a substantially transverse axis for carrying out angular corrections of the bone. There are provided a compression/distraction device movably coupleable with the clamps for carrying out longitudinal corrections of the bone. The orientably clamp is adjustable angularly in a predetermined geometric plane, as well as adjustable transversely for the group of bone screws carried by the clamp parallel to themselves for compensating the lateral movement induced by the angular correction.

24 Claims, 10 Drawing Sheets

U.S. PATENT DOCUMENTS

| | | |
|---|---|---|
| 4,621,627 | 11/1986 | DeBastiani et al. |
| 5,152,280 | 10/1992 | Danieli . |
| 5,160,335 | 11/1992 | Wagenknecht ........................ 606/59 |
| 5,207,676 | 5/1993 | Canadell et al. ....................... 606/54 |
| 5,292,322 | 3/1994 | Faccioli et al. ........................ 606/59 |
| 5,380,322 * | 1/1995 | Van Den Brink et al. ............ 606/57 |
| 5,728,096 | 3/1998 | Faccioli et al. ........................ 606/54 |
| 5,769,851 | 6/1998 | Veith ..................................... 606/57 |

* cited by examiner

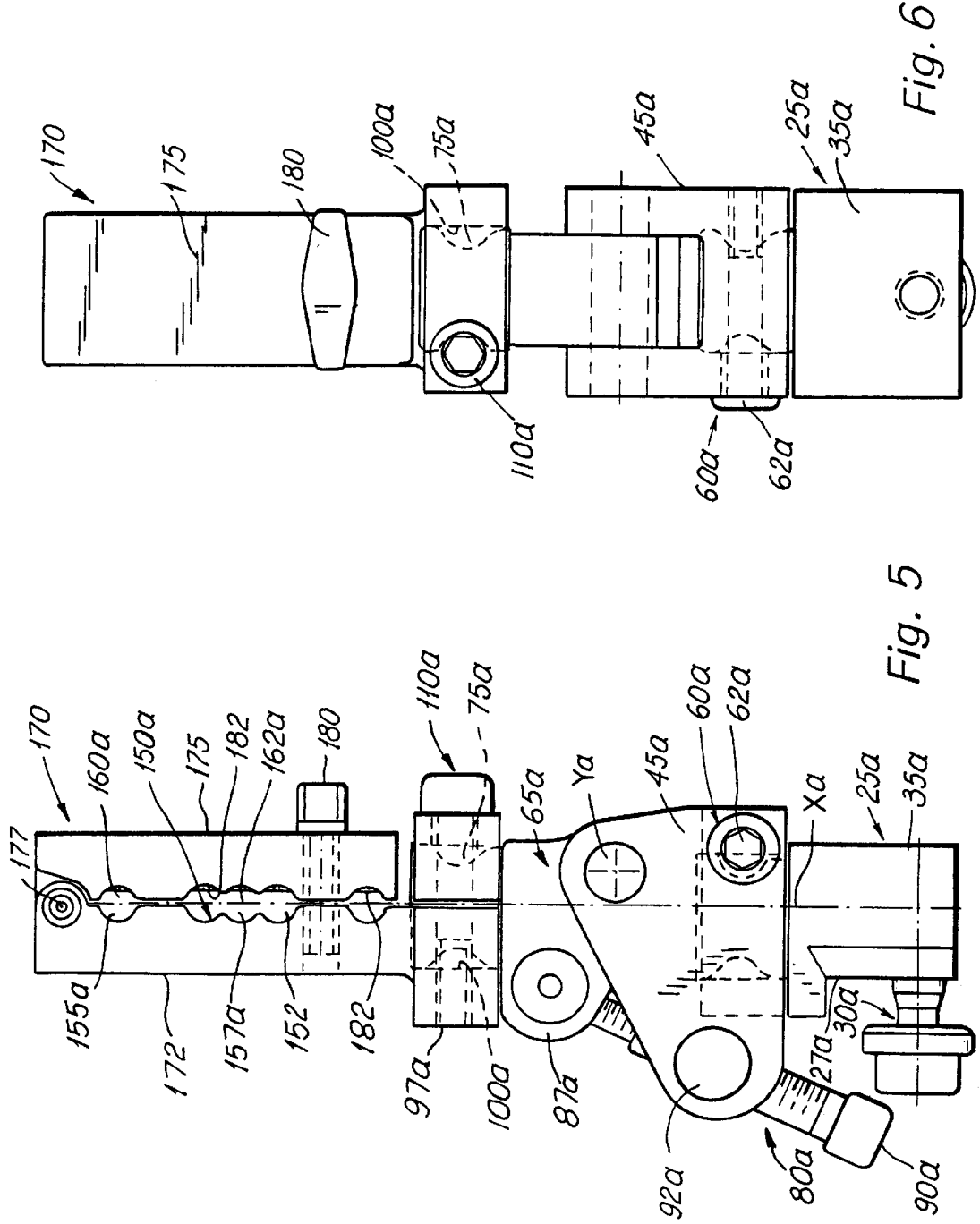

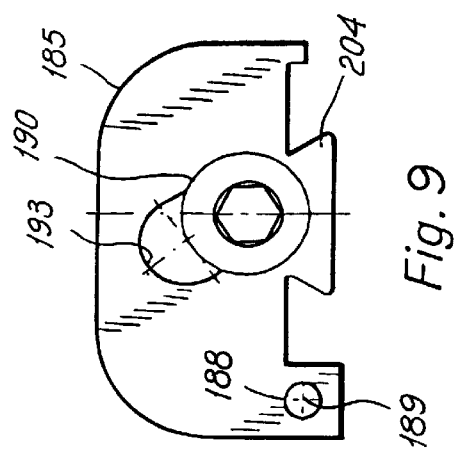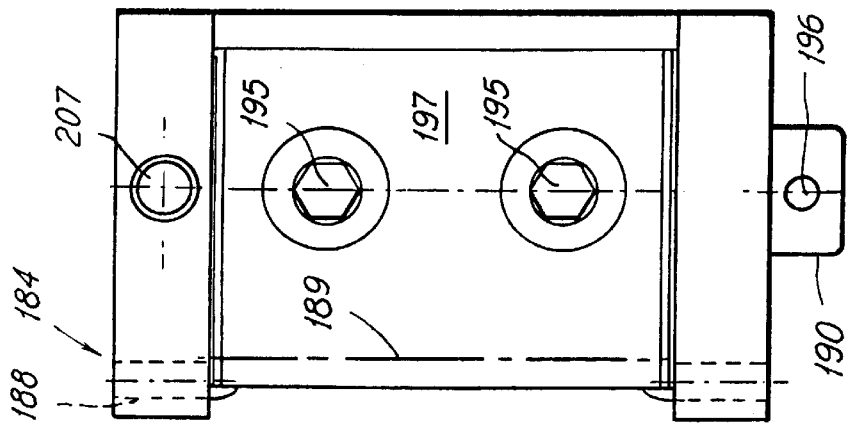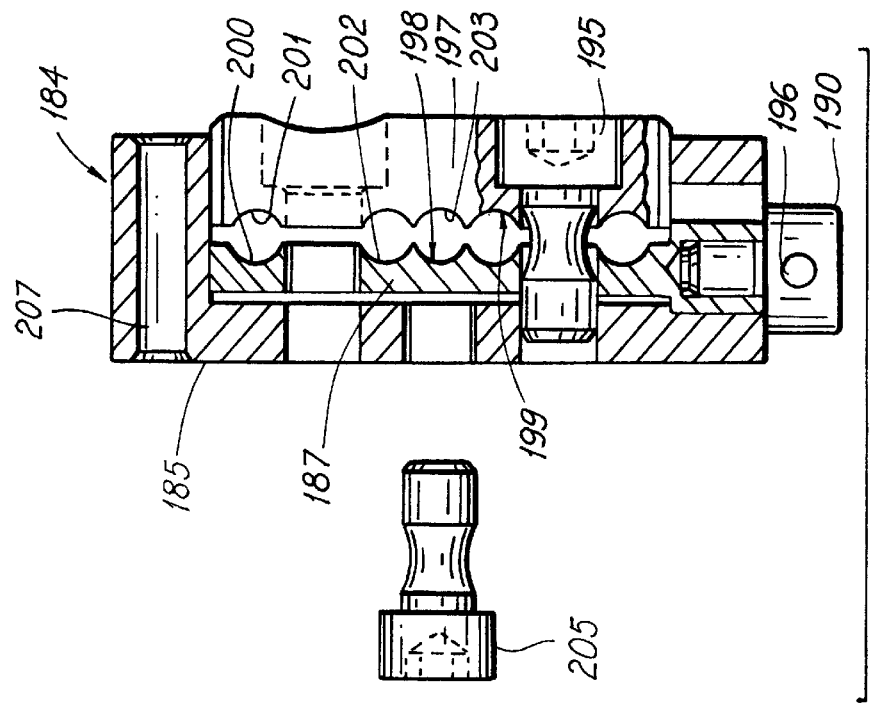

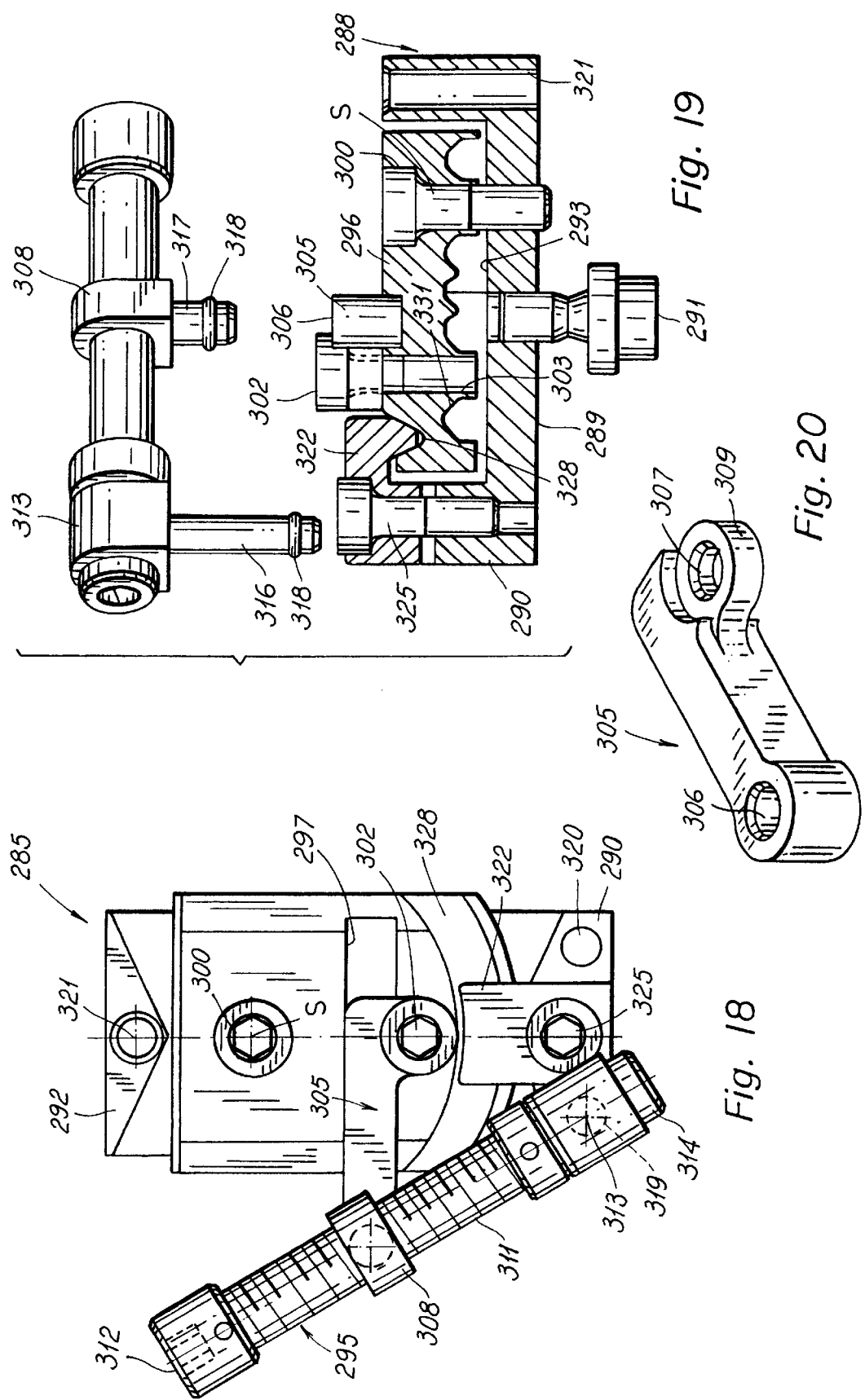

ORTHOPAEDIC DEVICE FOR THE GRADUAL CORRECTION OF LIMBS

BACKGROUND OF THE INVENTION

The present invention relates to an orthopaedic device for the gradual correction of limbs.

It is known that external fixation devices, adjustable in length and angular attitude, are commonly utilized for correcting certain angular and longitudinal defects of long bones of limbs. Such fixation devices essentially comprise clamps which hold groups of bone screws inserted in the portions of the bone affected by defects, such clamps being slidably mounted on elements or guides longitudinally positionable externally to the limb to be treated.

The correction is normally carried out gradually with the aid of compression/distraction devices which act on the mobile clamps while the bone callous regenerates itself permitting its manipulation until the desired correction is obtained.

One known device for the gradual correction of the limbs has a lateral clamp which allows an angular correction of the bone. Such known device has the drawback that the angular rotation induces a shifting of the screws in a transverse direction which renders the correction of the limb difficult.

BRIEF STATEMENT OF THE INVENTION

One principal aim of the present invention is to overcome the above described drawbacks providing an orthopaedic device which allows a complete correction in geometric planes which are also inclined with respect to the lateral and front-rear planes, in a gradual and easily controllable manner.

With this principal aim and others in view, there is provided an orthopaedic device for the gradual correction of angular and longitudinal defects of elongated bones, comprising at least one first clamp for a first group of screws insertable in a proximal portion of a bone, and at least one second clamp for a second group of screws insertable in a distal portion of the bone, a longitudinal guide bar positioned externally of the limb to be corrected for slidably supporting said first and second clamps in longitudinally distanced positions, at least one of said clamps being selectively orientable about a substantially transverse axis for carrying out angular corrections of the bone, there being provided compression/distraction means movably coupleable with said clamps for carrying out longitudinal corrections of the bone, characterized by the fact that said at least one orientable clamp has angular adjustment means in a predetermined geometric plane, as well as transverse adjustment means for the group of bone screws carried by said clamp parallel to themselves for compensating the lateral movement induced by the angular correction.

BRIEF DESCRIPTION OF THE DRAWINGS

The characteristics and advantages of the invention will become apparent from the following description of some preferred but not exclusive embodiments of an intramedullary cavity nail according to the invention, illustrated for illustrative and non-limiting purposes with the help of the attached drawing sheets in which:

FIG. 5 illustrates a front elevation view of a second embodiment of the proximal clamp assembly of FIG. 3, showing an alternative embodiment of proximal tray and proximal bone screw clamp;

FIG. 6 illustrates a side elevation view of the proximal clamp assembly of FIG. 5;

FIG. 7 illustrates a section view of an embodiment of the distal clamp assembly of FIG. 1 including a swivel clamp;

FIG. 8 illustrates a top plan view of the detail of FIG. 7;

FIG. 9 illustrates a lateral elevation view of the detail of FIG. 7;

FIG. 18 illustrates an enlarged elevational view of the distal clamp assembly of FIG. 16;

FIG. 19 illustrates a lateral section view of the detail of FIG. 18; and

FIG. 20 illustrates a perspective view of the reversible bracket of FIG. 19.

Corresponding reference characters indicate corresponding parts throughout the several views of the drawings.

DETAILED DESCRIPTION

Figure 1:
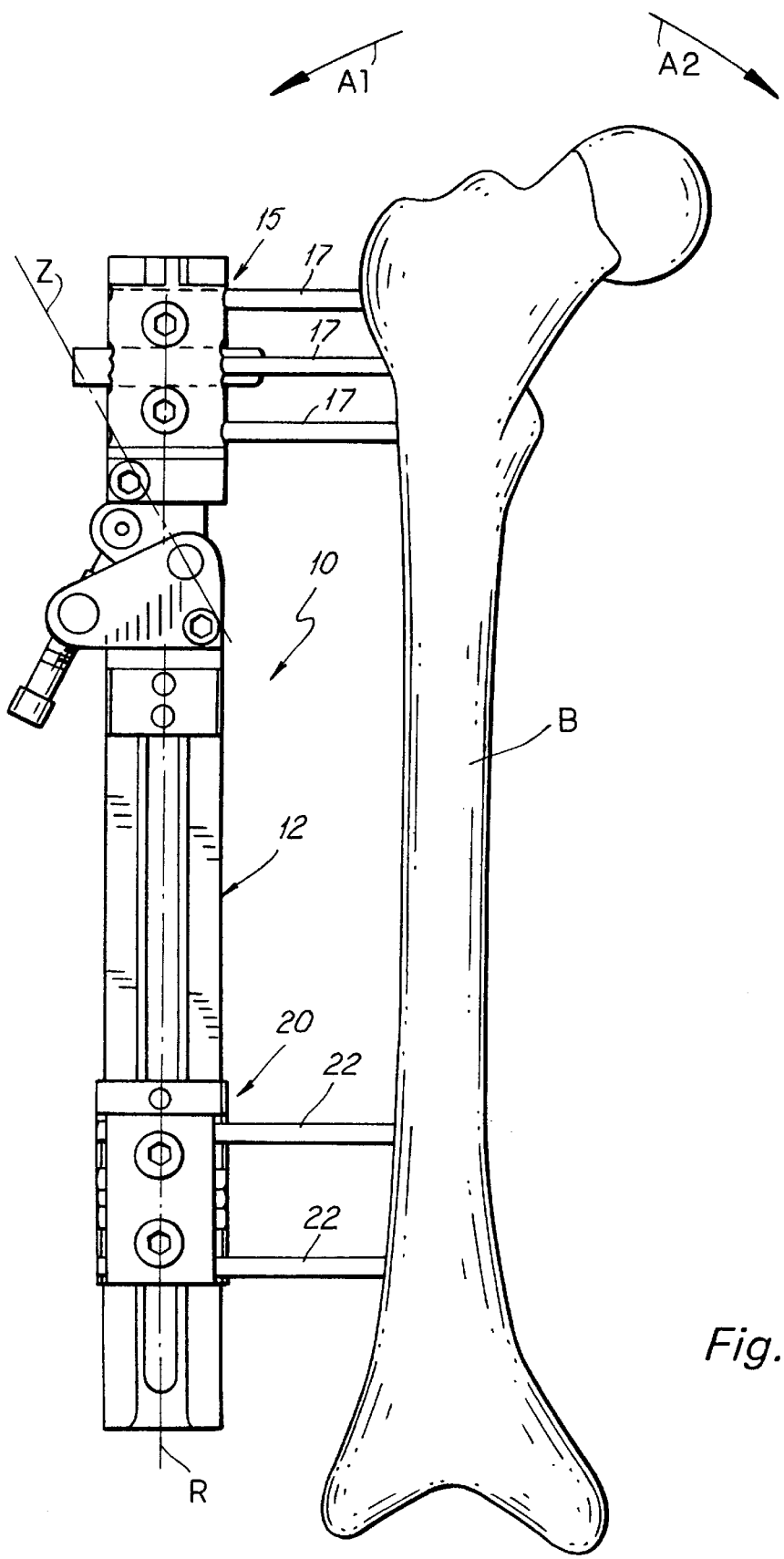
FIG. 1 is a view in front-elevation of a preferred orthopaedic device of the invention shown in application to a femur, in a lateral position, with arrows A1, A2 illustrating the transverse plane in which correction is made for a bone deformity.
Figures 3, 4:
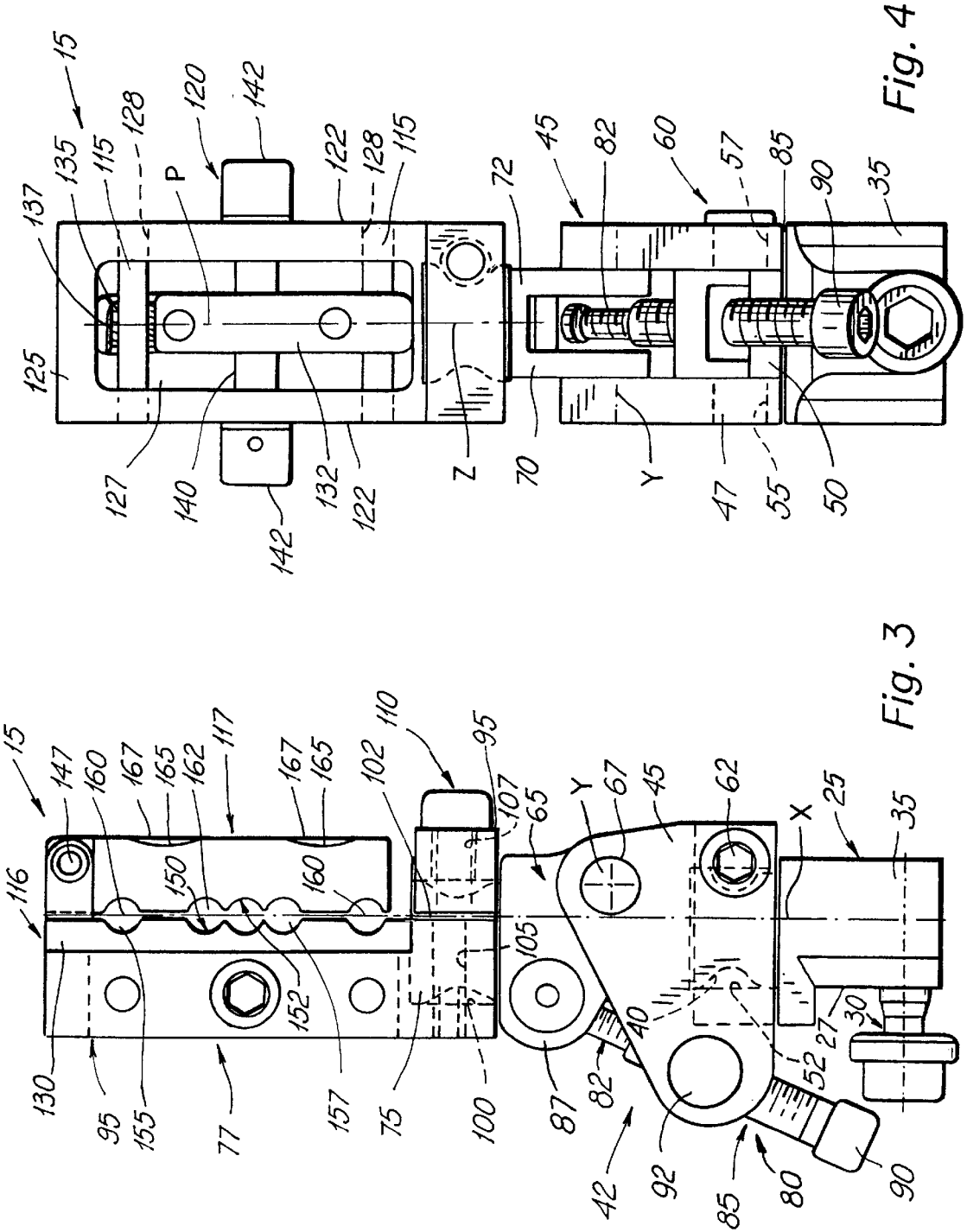
FIG. 3 illustrates an enlarged front elevation view of a proximal clamp assembly of FIG. 1.
FIG. 4 illustrates a lateral elevation view of the detail of FIG. 3.

In FIGS. 1 and 4 of the drawings, an orthopaedic device according to a preferred aspect of the invention, is generally indicated by the reference numeral 10. The device 10 is for the gradual correction of angular and/or longitudinal defects of elongate bones B, illustratively a femur in FIG. 1. Essentially, the device comprises a longitudinal guide bar or rail 12 of generally semicircular cross-section positioned externally to the limb to be corrected. The guide rail 12 mounts a first or proximal clamp assembly 15 for a first or proximal group of bone screws 17 insertable in a proximal portion of the bone B and a second or distal clamp assembly 20 for a second or distal group of bone screws 22 insertable in a distal portion of the bone.

Proximal Clamp Assembly

The proximal clamp assembly 15 comprises an attachment portion or proximal anchor 25 movably anchorable to the guide rail 12, for example by means of a dovetail proximal tenon 27, as shown in FIG. 3, coupleable to a complementary longitudinal cavity of the guide rail 12 and a locking or proximal rail screw 30. The upper end of proximal tenon 27 is outwardly flared to limit longitudinal translation of the proximal tenon in the longitudinal cavity of guide rail 12. Proximal rail screw 30 has a hexagonal head 32 (e.g., "Allen" head) rotatable by a complementary tool (e.g., "Allen" wrench).

The proximal anchor 25 includes a base portion 35 including proximal tenon 27 integrally formed therewith and a threaded bore into which proximal rail screw 30 is threaded. Also formed in base portion 35, above the threaded bore and parallel therewith, as viewed in FIG. 3, is a smooth bore in which a connection member of a compression/distraction device 37 may be inserted. An example of compression/distraction device 37 is disclosed in U.S. Pat. No. 4,621,627, the entire disclosure of which is hereby expressly incorporated by reference herein. The proximal anchor 25 also includes an integral upwardly extending anchor boss 40 with a reduced interior cross section for coupling to jack assembly 42, described hereinbelow.

Jack assembly 42, which is part of proximal clamp assembly 15, includes a lower jack bracket 45 rotatably coupled to proximal anchor 25 for rotation about a substantially longitudinal pivot or first axis X relative to a pivot plane P. Lower jack bracket 45 has a one-piece integral construction including a pair of generally triangular lower jack bracket sides 47 bridged by a substantially flat lower jack bracket web 50.

Lower jack bracket web 50 has a bracket socket 52 opening to the underside thereof. A portion of the wall of bracket socket 52 has a longitudinal bracket gap extending from the wall of the socket to the outer surface of lower jack bracket 45. A bracket locking bore having coaxial threaded and unthreaded sections 55, 57 extends through lower jack bracket 45 across the bracket gap and across a portion of bracket socket 52 in offset relation to the longitudinal axis thereof.

Coupling between lower jack bracket 45 and proximal anchor 25 is provided by placing the lower jack bracket on the proximal anchor so that anchor boss 40 is coaxially lodged in bracket socket 52, as shown in FIG. 3. First axis X is thereby defined by the coaxial longitudinal axes of anchor boss 40 and bracket socket 52.

A bracket locking screw 60, the end of which has threads corresponding to those in threaded section 55 of the bracket locking bore, is inserted through unthreaded section 57 and is screwed into the threaded section. The diameter of unthreaded section 57 is greater than that of the shaft of bracket locking screw 60 enabling the screw to translate through the unthreaded section of the bracket locking bore.

Bracket locking screw 60, when screwed into threaded section 55 of the bracket locking bore with anchor boss 40 lodged in bracket socket 52, extends transversely through the reduced inner portion of the anchor boss to obstruct removal of the boss from the bracket socket thereby preventing separation of lower jack bracket 45 from proximal anchor 25. Lower jack bracket 45 may swivel relative to proximal anchor 25 about first axis X if bracket locking screw 60 remains sufficiently loose that the bracket gap remains open.

Bracket locking screw 60 has a hexagonal head 62 (e.g., "Allen" head) rotatable by a complementary tool (e.g., "Allen" wrench). Tightening of bracket locking screw 60 closes the bracket gap clamping the walls of bracket socket 52 around anchor boss 40 to prevent relative swivelling about first axis X. Hexagonal head 62 seats in a countersunk portion of unthreaded section 57 of the bracket locking bore. Closure of the bracket gap may be visually detected enabling ready determination of locking of anchor boss 40.

For correction of angular defects, jack assembly 42 further comprises a body or upper jack bracket 65 hinged, by a jack pin 67. to lower jack bracket 45 on a substantially lateral or transverse axis Y defined by the central axis of jack pin 67. Upper jack bracket 65 has a one-piece integral construction including a pair of generally triangular upper jack bracket sides 70 bridged by an upper jack bracket web 72. Integrally formed on the upper surface of upper jack bracket web 72 is an integral upwardly extending upper bracket boss 75 with a reduced interior cross section for coupling to a proximal tray 77, described hereinbelow.

The transverse dimension between the outer surfaces of upper jack bracket sides 70 is slightly smaller than the transverse dimension between the interior surfaces of lower jack bracket sides 47 enabling insertion of the lower jack bracket sides between the upper jack bracket sides, as shown in FIG. 4. The lower and upper jack brackets 45, 65 are thereby disposed in generally mirror-image relation to one another with a transverse clearance therebetween enabling the pivoting of upper jack bracket relative to lower jack bracket about transverse axis Y in the pivot plane P.

The extent of angular-defect correction is micrometrically adjustable by means of a lead or differential screw assembly 80 having inner and outer screws 82, 85 in telescoping relation to one another. The solid shaft of inner screw 82 is externally threaded and the tubular shaft of outer screw 85 is externally and internally threaded. The internal threads of the shaft of outer screw 85 correspond with the external threads of the shaft of inner screw 82 allowing the outer screw shaft to be threaded onto the inner screw shaft such that, rotation of the outer screw relative to the inner screw results in translation of the outer screw shaft relative to the inner screw shaft. The internal and external threads of the shaft of outer screw 85 have different pitches.

Inner screw 82 has a first or hinge end 87, opposite the threaded coupling between the inner screw shaft and the shaft of outer screw 85, hinged to intermediate body or upper jack bracket 65 by a pin supported between upper jack bracket sides 70. Inner screw 82 is thereby allowed to pivot, without rotating, relative to upper jack bracket 65. Inner screw 82 may be further fixed longitudinally to upper jack bracket 65 by a pair of pins.

Outer screw 85 has a control end 90, opposite hinge end 87, defined by a hexagonal head (e.g., "Allen" head) rotatable by a complementary tool (e.g., "Allen" wrench). The central portion of the shaft of outer screw 85 has threaded engagement to a pivoted bracket nut 92 carried by lower jack bracket sides 47.

Rotation of control end 90 causes axial translation of outer screw 85 relative to bracket nut 92. Arrows may be printed on the curved side of the head on control end 90 indicating the direction of such translation resulting from a specific direction of rotation of the control end. For example, an arrow pointed toward bracket nut 92 and an arrow pointed in a clockwise direction, as viewed when facing the end of the head of control end 90, may be printed on the side of the head to indicate the direction of translation produced by such rotation.

Rotation of outer screw 85 also causes axial translation thereof relative to inner screw 82 in the opposite axial direction as compared to hinge end 87. For example, if clockwise rotation of control end 90, as viewed when axially facing the end thereof, causes the control end to translate toward bracket nut 92, then such rotation also causes the shaft of outer screw 85 to translate along the shaft of inner screw 82 away from hinge end 87. Consequently, rotating control end 90 alters the spacing between bracket nut 92 and hinge end 87 causing upper jack bracket 65 to tilt relative to lower jack bracket 45. The angular position of upper jack bracket 65 relative to lower jack bracket 45 may be visually detected by complementary gradation lines inscribed on the outer surfaces of lower jack bracket sides 47 and upper jack bracket web 72 sandwiched therebetween.

Proximal tray 77 comprises a substantially L-shaped support mounted to upper jack bracket 65 for rotatable adjustment about a substantially longitudinal angular pivot or second axis Z in the pivot plane P. Proximal tray 77 has a tray base 95 and foot 97, with the tray foot having a tray socket 100 opening to the underside thereof. A portion of the wall of tray socket 100 has a longitudinal tray gap 102 extending from the wall of the tray socket to the outer surface of tray foot 97. A tray locking bore having coaxial threaded and unthreaded sections 105, 107 extends through tray foot 97 across tray gap 102 and across a portion of tray socket 100 in offset relation to the longitudinal axis thereof.

Coupling between tray foot 97 and upper jack bracket 65 is accomplished in a similar manner as the coupling between lower jack bracket 45 and proximal anchor 25 provided by anchor boss 40 and bracket socket 52. Accordingly, a tray locking screw 110 having a hexagonal head 112, similar in construction to bracket locking screw 60, extends through the threaded and unthreaded sections 105, 107 of tray locking bore. Details of the coupling between tray foot 97 and upper jack bracket 65 may be had by reference to the description hereinabove for the coupling between lower jack bracket 45 and proximal anchor 25 provided by anchor boss 40 and bracket socket 52, in conjunction with FIGS. 3 and 4. The second axis Z is thereby defined by the coaxial longitudinal axes of bracket boss 75 and tray socket 100.

Proximal tray 18 has two transverse spines 115 for guiding a jaw or clamp base 116 of a proximal bone screw clamp 117 and a micrometric adjustment screw 120 for enabling controlled translation of the proximal bone screw clamp so as to compensate for lateral displacements induced by angular corrections. More specifically, tray base 95 is formed by a pair of tray sides 122 comprising integral elongate members extending upwardly from tray foot 97 in generally flush relation with the side of the tray foot to which tray socket 100 opens. The ends of tray sides 122 opposite tray foot 97 are spanned by a tray end 125 comprising an integral transverse member thereby defining a hollow rectangular tray interior 127. Spines 115 extend across tray interior 127 in transverse symmetrical relation to one another, as shown in FIG. 4. Spines 115, which may comprise pins, are longitudinally fixed in bores 128 in tray sides 122.

Proximal bone screw clamp 117 includes one piece clamp base 116 having a T-shaped cross section defined by a base seat 130 and clamp foot 132. Clamp base 116 is assembled to tray base 95 by inserting, with spines 115 removed, clamp foot 132 into tray interior 127, as shown in FIG. 4. Clamp foot 132 has a pair of transverse bores 135 which, when base seat 130 is placed on tray base 95 as shown in FIG. 3, coaxially align with bores 128 in tray sides 122. Coaxially mounted in bores 135 of clamp foot 132 are annular bushings 137 through which spines 115 extend. With clamp foot 132 inserted in tray interior 127 and bores 128, 135 coaxially aligned, as shown in FIG. 4, spines 115 are inserted through respective sets of the coaxially aligned bores and longitudinally anchored in tray sides 122.

Bores 135 in clamp foot 132 are spaced from base seat 130 such that, when spines 115 are inserted through the bores in the clamp foot, a slight clearance is established between the base seat and tray base. Similarly, a slight clearance is established between one edge of clamp foot 132 and tray end 125, and between the other edge of the clamp foot and tray foot by virtue of the length of the clamp foot being slightly less than that of tray interior 127. This, along with the slidable engagement between the clamp foot 132 and spines 115 provided by bushings 137, allows clamp base 116 to translate relative to tray base 95 in a direction parallel to the axis of the spines.

Micrometric adjustment screw 120 having a threaded shaft 140 extending through a correspondingly threaded bore in clamp foot 132 midway between spines 115, and through unthreaded bores in tray sides 122. Fixed to opposite ends of shaft are hexagonal heads 142 (e.g., "Allen" heads) rotatable by a complementary tool (e.g., "Allen" wrench). Washers may be located between heads 142 and tray sides 122.

Rotation of shaft 140 causes clamp foot 132 to ride along the shaft, due to the threaded engagement between the clamp foot and shaft, thereby producing transverse translation of clamp base 116 relative to tray base 95. Arrows may be printed on the curved sides of heads 142 indicating the translation direction resulting from a specific rotation direction thereof. For example, clockwise rotation of each head 142, as viewed when facing the outer end of the heads, may cause translation of clamp foot 132 toward the head being viewed. Such directions may be indicated by arrows on the respective heads 142.

Shaft 140 may be tensioned to produce friction between heads 142 and tray sides 122 to resist rotation of the shaft. Rotation of heads 142 may therefore require substantial force resulting in clamp base 116, without rotation force being applied to heads 142, being locked in place relative to tray base 95.

Tray end 125 may have a series of equally spaced transverse gradation lines inscribed along the edge of the outer surface thereof adjacent to clamp base 116. The series of gradation lines may be midway between ends of tray end 125 with the central gradation line marked "0". A complementary single gradation line may be inscribed on the adjacent edge of clamp base 116 midway between the edges thereof to provide a means for measuring the displacement of the clamp base relative to tray base 95.

Proximal bone screw clamp 117 also includes a proximal cover 145 hinged to base seat 130 by a hinge pin 147. Base seat 130 and proximal cover 145 have complementary facing proximal seats 150, 152 for supporting bone screws 17. Proximal seat 150 includes two elongate arcuate outer recesses 155 and three elongate arcuate inner recesses 157 all of which are parallel to one another, as shown in FIG. 3. Inner recesses 157 adjoin one another to define a scalloped cross section. Outer recesses 155 are transversely symmetrical relative to inner recesses 157. Outer and inner recesses 155, 157 are complemented by outer and inner recesses in proximal seat 152.

A pair of bores 165, equally spaced from the ends of proximal cover 145, extend from the apex of the proximal cover through proximal seats 150, 152 and clamp foot 132, as shown in FIGS. 3 and 4. Proximal clamp screws 167 having threaded shafts are inserted through bores 165 in proximal cover 145 and into engagement with correspondingly threaded bores in clamp base 116. Proximal clamp screws 167 have hexagonal heads (e.g., "Allen" heads) rotatable by a complementary tool (e.g., "Allen" wrench). Proximal cover 145 may thereby be clamped to clamp base 116, as shown in FIG. 3. When proximal clamp screws 167 are fully inserted into bores 165 in proximal cover 145, the hexagonal heads of the screws seat in countersunk ends of the bores in the proximal cover.

Bores 165 in proximal cover 145 are unthreaded and a radial clearance exists between the shafts of proximal clamp screws 167 and the bores in cover 145. Hinge pin 147 extends through a slot in proximal cover 145 transverse to proximal seat 152. As a result, limited transverse displacement of proximal cover 145 relative to base seat 130, equal to the length of the slot, is possible with proximal clamp screws 167 inserted into through bores 165 in the proximal cover and clamp base 116.

FIGS. 5 and 6 illustrates an alternative embodiment of proximal clamp assembly 15a which is similar to proximal clamp assembly 15 with the substitution of proximal bone screw clamp 170 for proximal tray and bone screw clamp 77, 117 of FIGS. 1 to 4. Accordingly, the parts of proximal clamp assembly 15a corresponding to proximal clamp assembly 15 are represented by the reference characters used in FIGS. 1 to 4 with the addition of the suffix a in FIGS. 5 and 6.

Proximal bone screw clamp 170 includes a base foot 97a corresponding to tray foot 97 of proximal tray 77. Accordingly, the parts of base foot 97a corresponding to tray foot 97 are represented by the reference characters used in FIGS. 1 to 4 with the addition of the suffix a in FIGS. 5 and 6. Base foot 97a is coupled to upper jacket bracket 65a in a similar manner as the coupling between tray foot 97 and upper jack bracket 65. Details about this coupling, and the lockable rotation provided thereby, may be had from the description of the coupling between tray foot 97 and upper jack bracket 65, hereinabove.

Proximal bone screw clamp 170 includes a proximal clamp base 172 upwardly extending from integral base foot 97a, as viewed in FIGS. 5 and 6. A proximal cover 175 is hinged to proximal clamp base 172 by a pin 177 to swing between open and closed positions, the latter of which is shown in FIG. 5. Proximal cover 175 is locked in the closed position by a proximal clamp screw 180 having a threaded shaft screwable into a correspondingly threaded bores in the proximal cover and proximal clamp base 172, as shown in FIG. 5.

Proximal clamp base and cover 172, 175 have a proximal seats 150a, 152a corresponding to proximal seats 150a, 152a. Accordingly, the parts of proximal seats 150a, 152a corresponding to proximal seats 150, 152 are represented by the reference characters used in FIGS. 2 and 3 with the addition of the suffix a in FIG. 5.

Proximal cover 175 has longitudinal front and rear cover grooves each of which has closed ends with a circular cross section and an intermediate portion, with an arcuate cross section, between the ends. The cover grooves open into proximal seat 152a. Rubber is injected into the cover grooves and, upon hardening, forms rods, longitudinal portions of which extend beyond proximal seat 152a resulting in formation of a pair of rubber cover ridges 182, one of which is shown in FIG. 5. The rubber of cover ridges 182 is formed of a material which may be sterilized.

When proximal cover 175 is clamped to proximal clamp base 172 with proximal bone screws 17 therebetween, cover ridges 182 are compressed between the cover and bone screws, for gripping thereof, thereby to resist translation of the bone screws relative to proximal bone screw clamp 170.

Distal Clamp Assembly

Distal clamp assembly 20 may be a clamp assembly of the standard type for bone screws. Alternatively, distal clamp assembly 20 may of the swivelling type such as swivel clamp assembly 184 seen in FIGS. 7 to 9, which is normally positioned in a distal or medial position along guide rail 12.

Swivel clamp assembly 184 is formed by a support plate 185 anchorable to the guide bar 12, upon which a first jaw 187 of the clamp is hinged by a pin 188 about a substantially longitudinal axis 189. Locking screw 190 extends through an arcuate eyelet hole 193 into threaded engagement with first jaw 187 such that the arcuate eyelet hole allows swivelling of first jaw 187 relative to support plate 185 about axis 189.

Locking screw 190 has a hexagonal head (e.g., "Allen" head) rotatable by a complementary tool (e.g., "Allen" wrench). The head of locking screw 190 also has a radial hole 196 into which an elongate tool may be inserted for its screwing in case of limited space for the surgeon. First jaw 187 is locked in a desired inclination relative to support plate 185 by locking screw 190.

A second jaw 197 is locked on the first jaw 187 by means of locking screws 195. Both first and second jaws 187, 197 have transverse complementary first and second bone screw seats 198, 199 for accommodating the bone screws 22. First and second bone screw seats 198, 199 each include two elongate arcuate outer recesses 200, 201 and three elongate arcuate inner recesses 202, 203 all of which are parallel to one another, as shown in FIG. 7. Respective sets of inner recesses 202, 203 adjoin one another to define scalloped cross sections. Outer recesses 200, 201 are transversely symmetrical relative to respective sets of inner recesses 202, 203.

The support plate 185 has means for longitudinally adjustable connection to the guide rail 12; as shown, constituted by a dovetail tenon 204 engageable, before the mounting of the other clamp, in a countershaped cavity formed along the guide rail, and by a stop screw 205 passing through a longitudinal groove of the guide rail. Support plate 185 has a smooth connection bore 207 in which a connection member of a compression/distraction device, such as compression/distraction device 37, discussed hereinabove, may be inserted to position the support plate along guide rail 12.

Figure 11:
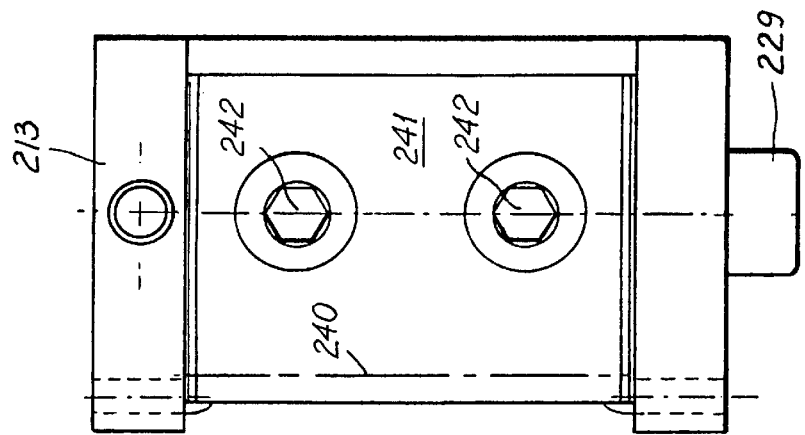
FIG. 11 illustrates a top plan view of the detail of FIG. 10.
Figure 10:
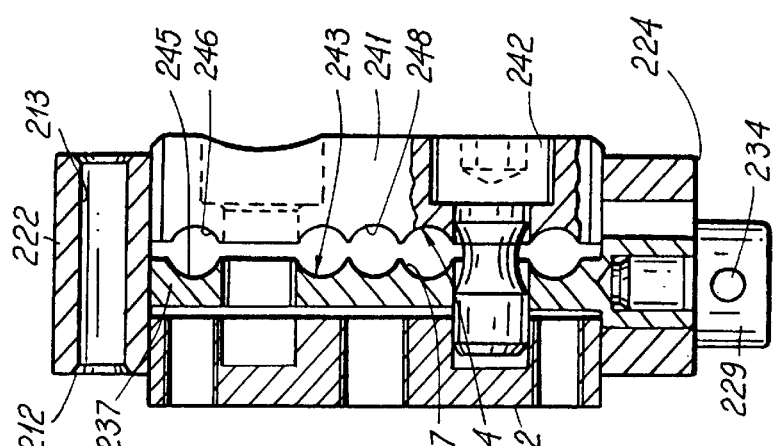
FIG. 10 illustrates a section view of a second variation of the swivel clamp of FIG. 7.
Figure 12:
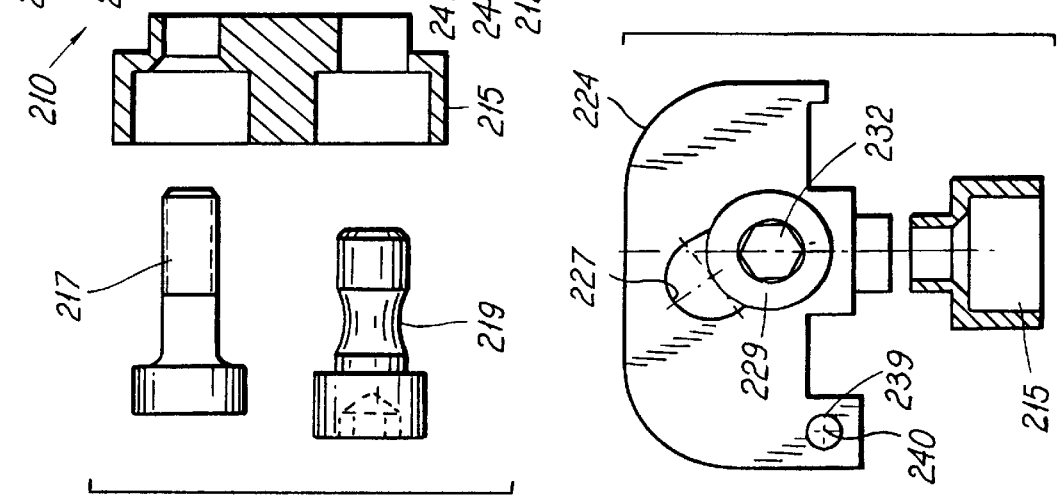
FIG. 12 illustrates a lateral elevation view of the detail of FIG. 10.

FIGS. 10 to 12 show an alternative embodiment of the swivel clamp assembly 184 illustrated in FIGS. 7 to 9. In swivel clamp assembly 210, the connection means of the support plate 212 to the guide rail 12 are constituted by a connecting block 215 anchored to the guide rail by means of screws 217, 219 of which one serves to anchor the block allowing it to slide along the groove, while the other serves to block the longitudinal movement of the support plate. Support plate 212 has a smooth connection bore 213 in which a connection member of a compression/distraction device, such as compression/distraction device 37, discussed hereinabove, may be inserted to position the support plate along guide rail 12.

The support plate 210 has two end supports 222, 224 one of which has an arcuate eyelet hole 227 in which there passes a screw 229 with a hexagonal fitting 232 (e.g., "Allen" head) rotatable by a complementary tool (e.g., "Allen" wrench). Hexagonal fitting 232 also has a radial hole 234 into which an elongate tool may be inserted for its screwing in case of limited space for the surgeon.

A first jaw 237 of the clamp is hinged by a pin 239 about a substantially longitudinal axis 240. Arcuate eyelet hole 227 allows swivelling of first jaw 237 relative to support plate 212 about axis 240. First jaw 237 is locked in a desired inclination relative to support plate 212 by screw 229.

A second jaw 241 is locked on the first jaw 237 by means of locking screws 242. Both first and second jaws 237, 241 have transverse complementary first and second bone screw seats 243, 244 for accommodating the bone screws 22. First and second bone screw seats 243, 244 each include two elongate arcuate outer recesses 245, 246 and three elongate arcuate inner recesses 247, 248 all of which are parallel to one another, as shown in FIG. 10. Respective sets of inner recesses 247, 248 adjoin one another to define scalloped cross sections. Outer recesses 245, 246 are transversely symmetrical relative to respective sets of inner recesses 247, 248.

Thanks to its possibility of being able to swivel, the swivel clamp assemblies 184, 210 illustrated in FIGS. 7 to 11 may be inclined allowing for the bone screws 22 to be screwed into the bone B also in case of notable curvature of the same, without having to move the clamps excessively towards the end of the guide rail 12.

Figure 15:
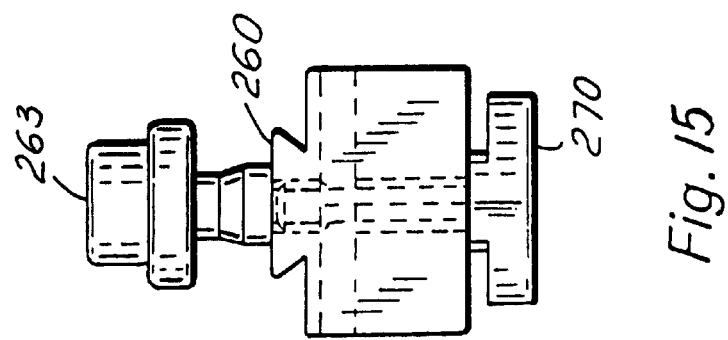
FIG. 15 illustrates a top plan view of the detail of FIG. 13.
Figure 14:
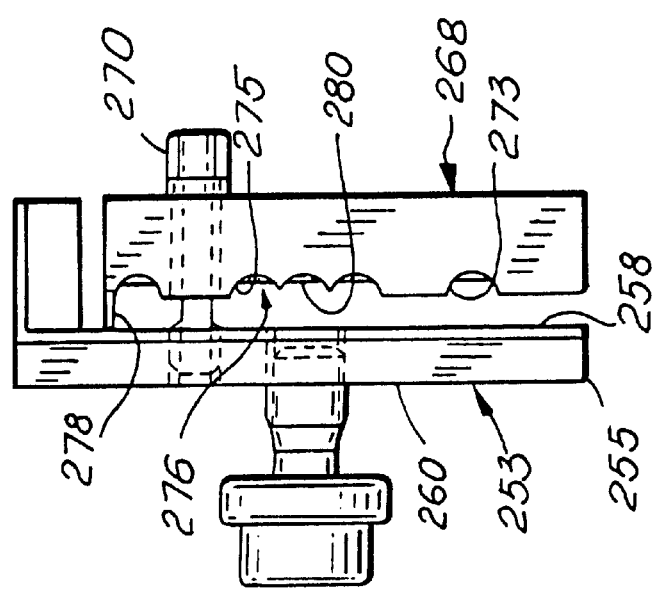
FIG. 14 illustrates a side elevation view of the detail of FIG. 13.
Figure 13:
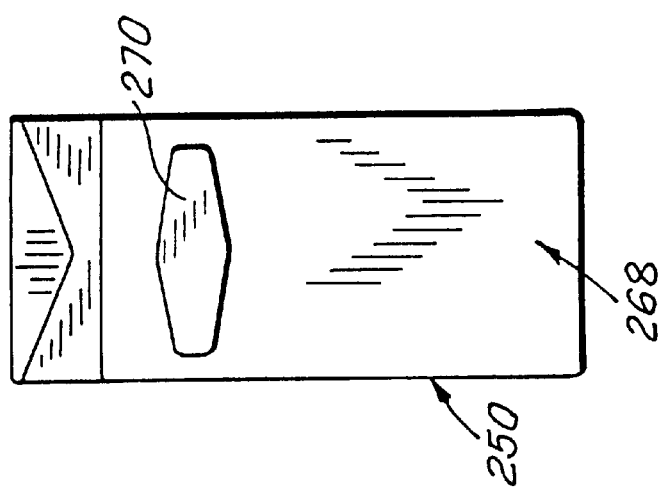
FIG. 13 illustrates an enlarged view of an embodiment of the distal clamp assembly of FIG. 1 including a cantilevered clamp assembly.
Figure 16:
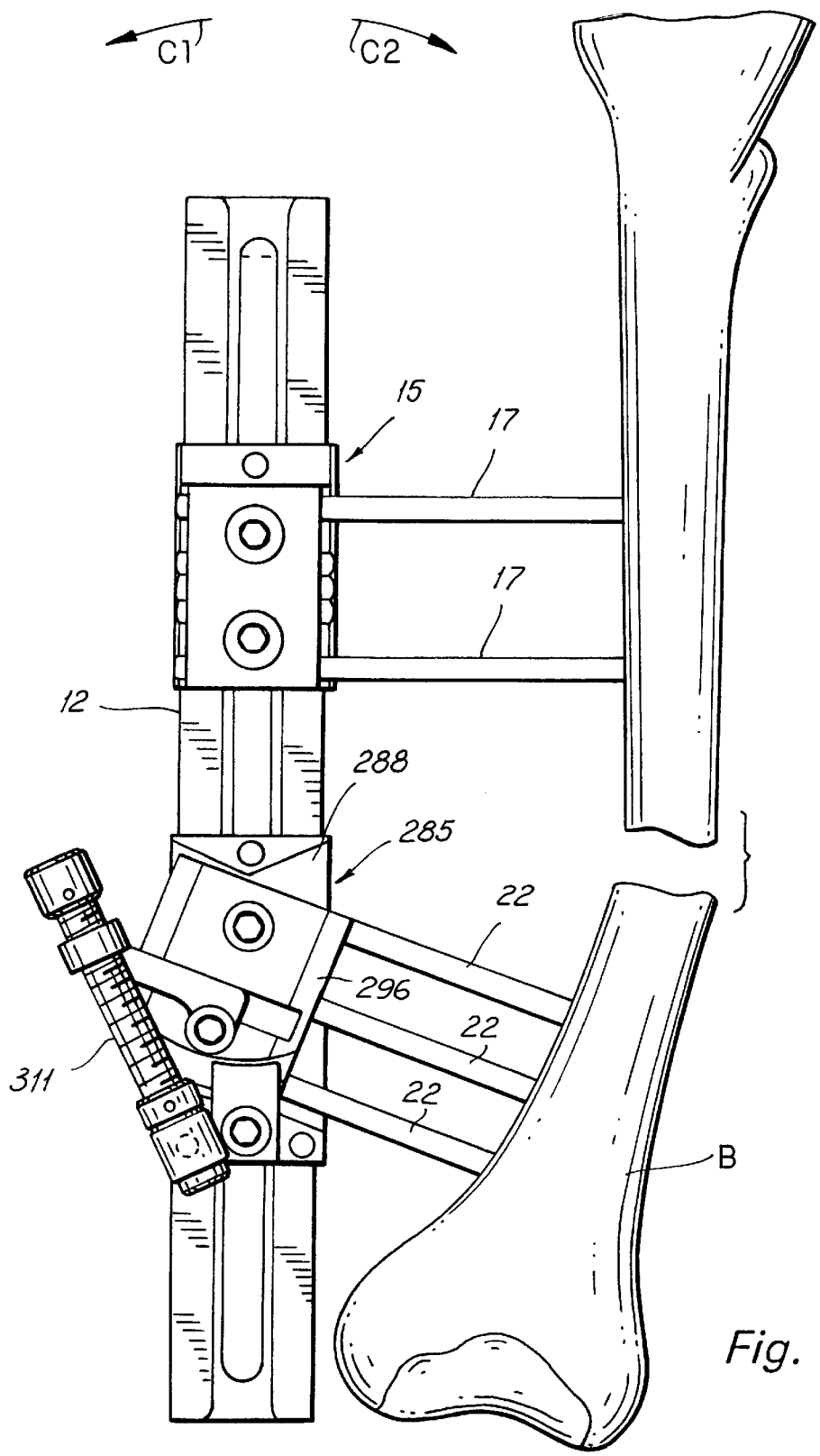
FIG. 16 is a view similar to FIG. 1, but on an enlarged scale, of alternative embodiments of the proximal and distal clamp assemblies of FIG. 1 shown in application to a femur, in a lateral position, with arrows C1, C2 illustrating the transverse plane in which correction is made to an angular defect of a femur and the femur being broken to illustrate a phase of correcting the angular defect.
Figure 17:
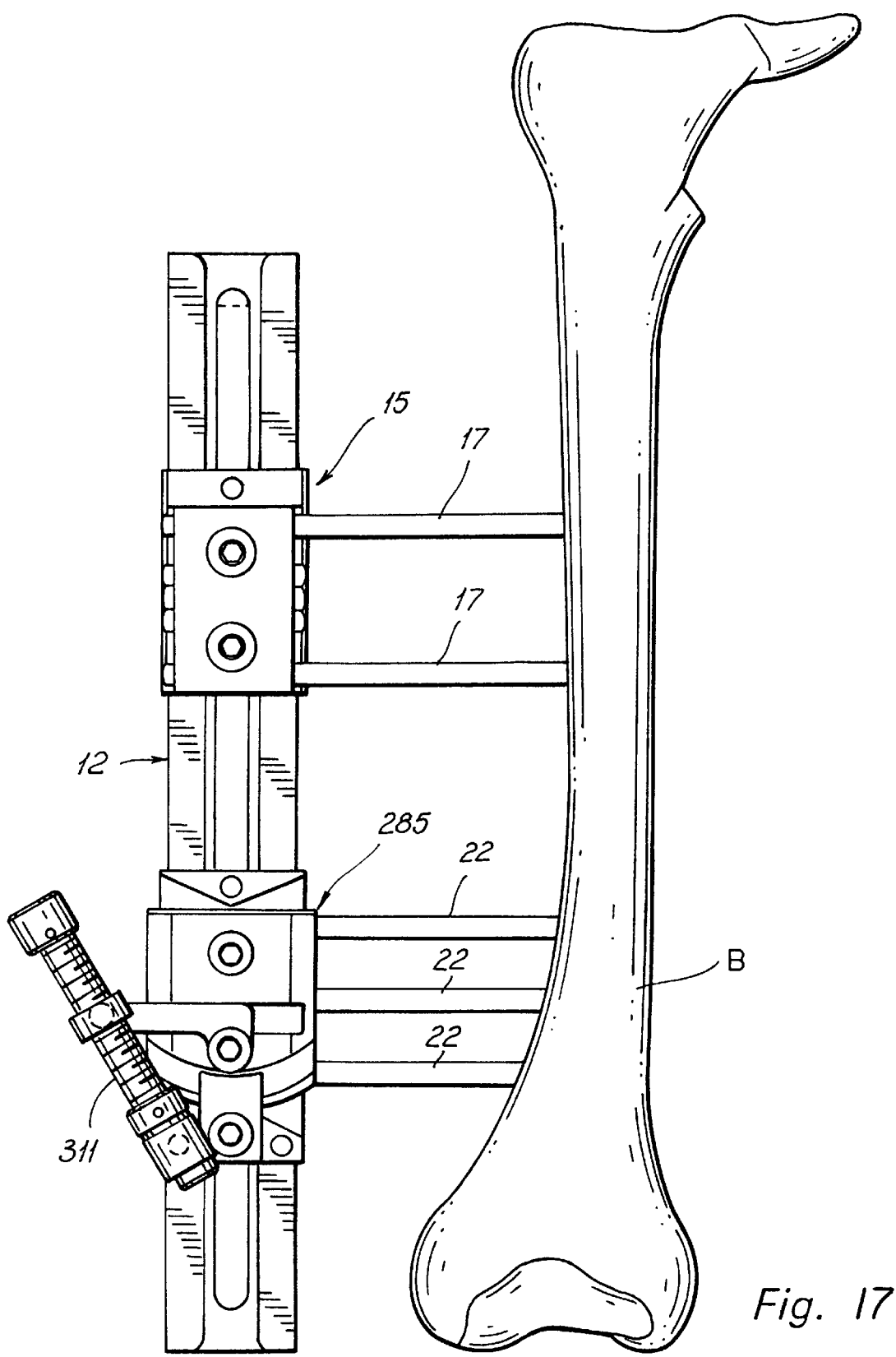
FIG. 17 is a similar view of the orthopaedic device of FIG. 16, but on a reduced scale, at completion of the correction.

FIGS. 13 to 15 illustrate another alternative embodiment of distal clamp assembly 20 comprising a cantilevered clamp assembly 250 including an L-shaped clamp base 253 having a base plate 255 with a support face 258 and an integral dovetail distal tenon 260 formed on the opposite face thereof. Distal tenon 260 has a complementary shape to longitudinal cavity in guide rail 12 enabling clamp base 253 to longitudinally translate along the guide rail when coupled thereto. Distal tenon 260 may be locked to guide rail 12 by inserting a rail locking screw 263 into a threaded bore in base plate 255 such that the guide rail is between the head of the locking screw and the base plate, and tightening the locking screw so the head thereof and the base plate are clamped against opposite sides of the guide rail.

Cantilevered clamp assembly 250 includes a cover 268 connectable to base plate 255 by clamp locking screw 270 having a shaft with a threaded end complementing threaded bores in the cover and base plate. The shaft of clamp locking screw 270 has an unthreaded intermediate portion between the threaded end and head thereof. The bore in cover 268 through which clamp locking screw 270 extends has threads complementing the threads in the end of the clamp locking screw. The unthreaded intermediate portion of clamp locking screw 270 is sized to provide a radial clearance between the unthreaded portion and the bore in cover 268 allowing rotation of the cover relative to base plate 255 about the central axis of clamp locking screw 270. This allows outer and inner recesses 273, 275, described hereinbelow, to be oriented with various inclinations relative to a transverse central plane perpendicular to support face 258 enabling distal bone screws 22 having corresponding inclinations to be clamped between cover 268 and base plate 255.

Outer and inner recesses 273, 275 define bone screw seats 276 for accommodating the bone screws 22. The two outer recesses 273 are each elongate arcuate recesses and the three inner recesses 275 are each elongate arcuate recesses, all of which are parallel to one another as shown in FIG. 14. Inner recesses 275 adjoin one another to define scalloped cross sections. Outer recesses 273 are transversely symmetrical relative to inner recesses 275.

Cover 268 has an integral transverse lip 278 extending inwardly from one of the outer recesses 273, as shown in FIG. 14. When clamp locking screw 270 is screwed into base plate 255 sufficiently so that the end of lip engages support face 258, cover 268 becomes cantilevered about the engagement between the lip and screw seat. This equalizes the clamping force between cover 268 and base plate 255 produced by clamp locking screw 270, which is offset relative to the transverse central axis of the cover.

Cover 268 has longitudinal front and rear cover grooves each of which has closed ends with a circular cross section and an intermediate portion, with an arcuate cross section, between the ends. The cover grooves open into cover seat including outer and inner recesses 273, 275. Rubber is injected into the cover grooves and, upon hardening, forms rods, longitudinal portions of which extend beyond the cover seat resulting in formation of a pair of rubber cover ridges 280, one of which is shown in FIG. 14. The rubber of cover ridges 280 is formed of a material which may be sterilized.

Base plate 255 has an integral stop 283 extending inwardly from support face 258 of base plate 255, as shown in FIG. 14. Stop 283 has a triangular cross section which limits the rotation of cover 268 relative to base plate 255 about the central axis of clamp locking screw 270 providing a minimum overlap between screw seats 276 and support face 258 to adequately support distal bone screws 22 clamped therebetween.

FIGS. 16 to 19 illustrate another alternative embodiment of distal clamp assembly 20 in a second embodiment of the invention of FIG. 1. In this embodiment, proximal clamp assembly 15 may be a clamp assembly of the standard type for bone screws, oscillating clamp assembly 285, of an oscillating type, is constituted by a base 288 anchorable to guide rail 12 by means of a screw 291. Base web 289, described hereinbelow, may also have a tenon, similar to distal tenon 260 shown in FIGS. 14 and 15, to provide additional anchoring to guide rail 12.

Base 288 includes a base web 289 having a substantially flat external surface or base seat 293, and opposing base legs 290, 292. Base leg 290 has a pair of smooth mounting bores 319, 320 for supporting screw 311, described hereinbelow. Base leg 292 has a triangular cross section and a smooth mounting bore 321 into which a connection member of a compression/distraction device, such as compression/distraction device 37, discussed hereinabove, may be inserted to position base 288 along guide rail 12.

Oscillating clamp assembly 285 includes a bone screw clamp assembly 295 having a cover 296 which is oscillatingly mounted on the flat base web 289 about an axis S substantially perpendicular to the longitudinal axis of guide rail 12. Cover 296 is joined to base web 289 by a hinge screw 300 the central axis of which coincides with axis S. The outer face of cover 296 has a transverse groove 297 with a U-shaped cross section.

To the cover 296 there is fixed by means of a screw 302 a reversible bracket 305 to whose end is hinged an internally threaded ring 308 in which is engaged a screw 311 having an end held axially by a sleeve 313 with a radial pin 316 insertable in a hole or mounting bore 319 provided in the base leg 290. Ring 308 has a radial pin 317 insertable in bore 306 in reversible bracket 305. Radial pins 316, 317 each have annular grooves in which are seated resilient O-rings 318 to resist removal of the pins from respective bores 319, 320, 306.

Screw 302 is threaded through a correspondingly threaded bore 303 in cover 296. The screw 311 has both ends with hexagonal set heads 312, 314 in order to allow to control it from both sides. The hexagonal set heads 312, 314 (e.g., "Allen" head) may be rotatable by a complementary tool (e.g., "Allen" wrench).

Reversible bracket 305 includes an elongate member having a rectangular cross section complementing the groove 297 in cover 296. The end of reversible bracket 305 opposite bore 306 has a transversely recessed finger 309 in which is formed a transverse bore 307, as shown in FIG. 20. The transverse recess of finger 309 is slightly less than the depth of groove 297 enabling reversible bracket 305 to be lodged in groove 297, as shown in FIGS. 18 and 19, with the side of finger 309 in mating engagement with cover 296. Screw 302 is may then be inserted through bore 307 into a threaded bore in cover 296. Rotation of either head 312, 314 causes axial translation of the externally threaded shaft thereof relative to internally threaded ring 308. In contrast, rotation of screw 311 in sleeve 313 does not result in such relative axial translation of the screw. Cover 296 thereby pivots relative to base 288 about axis S as a result of reversible bracket 305 being fixed relative to cover 296 in the plane of rotation and pin 316 being inserted into bore 319. Rotation of screw 311 in the opposite direction causes cover 296 to pivot in the opposite direction resulting in the oscillating feature of oscillating clamp assembly 285.

Arrows may be printed on the curved sides of head 312 and sleeve 313 indicating the direction of translation of ring 308 resulting from a specific direction of rotation of heads 312, 314. For example, an axial arrow pointed toward the face of head 312 and an arrow pointed in a clockwise direction, as viewed when facing the end of the head, may be printed on the side of the head to indicate the direction of translation of the ring produced by such rotation.

An alternative orientation of screw 311 relative to base 288, as shown in FIG. 18, may be achieved by transferring pin 316 from bore 319 to bore 320. A further alternative orientation may result from removing screw 302 from cover 296, turning over reversible bracket 305 so that bore 307 therein aligns with bore 303 in cover 296 such that the elongate member of the reversible bracket extends rightwardly from bore 303, as viewed in FIG. 18. Pin 317 is then inserted into bore 306, with pin 316 being inserted in either bore 319 or 320. The reversibility of reversible bracket 305 provides right- and left-hand operation of screw 311.

For locking the cover 296 in the pre-established angular position, there is provided a stop 322 anchored to the base leg 290 by means of a screw 325 and having a cuneiform end which engages against the bottom of a circular cavity 328 with a bottom substantially countershaped with respect to the stop 322, formed on the external face of the cover. In such a manner it is possible to exert notable locking forces rendering the orientation of the clamp more reliable and secure.

The cover 296 has on its internal face which faces the base seat 293 of base web 289 five transverse seats 331 for the bone screws 22, with transverse cross section of greater value than the maximum diameter of the screws and with a Vshaped bottom for permitting the sliding of the screws 22 parallel to themselves in case of loosening of the cover 296. The triangular cross section of base leg 292 limits the rotation of cover 296 relative to base 288 about axis S providing a minimum overlap between transverse seats 331 and base seat 293 to adequately support distal bone screws 22 clamped therebetween. The angular position of cover 296 relative to base 288 may be visually detected by gradation lines inscribed on the outer surface of the cover.

All of the clamps have holes for the insertion of controlling ends of compressors/distractors in order to carry out an elongation of the bones.

Operation

Proximal bone screw clamp 117, shown in FIGS. 1 to 4, swivel clamp assemblies 184, 210, shown in FIGS. 7 to 12, and oscillating clamp assembly 285, shown in FIGS. 16 to 20, typically clamp to bone screws 17, 22. Proximal bone screw clamp 170, shown in FIGS. 5 and 6, and cantilevered clamp 10 assembly 250, shown in FIGS. 13 to 14, may clamp to bone screws 17, 22, drill guides and screw guides, depending on the application. A screw guide is tubular having a typical outer diameter of 8 mm. The inner diameter of a screw guide is slightly larger than the outer diameter of a drill guide or bone screw 17, 22, typically 6 mm, allowing insertion of either into the screw guide. A drill guide is tubular having an inner diameter which is slightly larger than a drill bit, which is sized to drill holes, typically 4.8 mm diameter, into bone B into which bone screws 26, typically 6 mm diameter, threadedly engage.

An advantage of screw guides is that, if the orthopaedic device 10 is used to position drill guides for boring holes in bone B, the drill guides may be removed from the screw guides after such boring and replaced with bone screws 17, 22 without having to open the bone screw clamps, for example proximal bone screw clamp 170, or otherwise disturb the clamp assemblies, for example proximal clamp assembly 15a, shown in FIGS. 5 and 6. Orthopaedic device 10 may then be used to manipulate bone B.

Orthopaedic device 10, with drill guides clamped in proximal bone screw clamp 170, shown in FIGS. 5 and 6, or cantilevered clamp assembly 250, shown in FIGS. 13 to 14, may be advantageously used to drill holes in the proximal and distal portions of bone B at preselected angles for insertion of bone screws 17, 22, therein at such angles. Such preselected angles may be achieved by manipulating proximal bone screw clamp 170 about axes X, Y, Z, as described hereinbelow.

Figure 2:
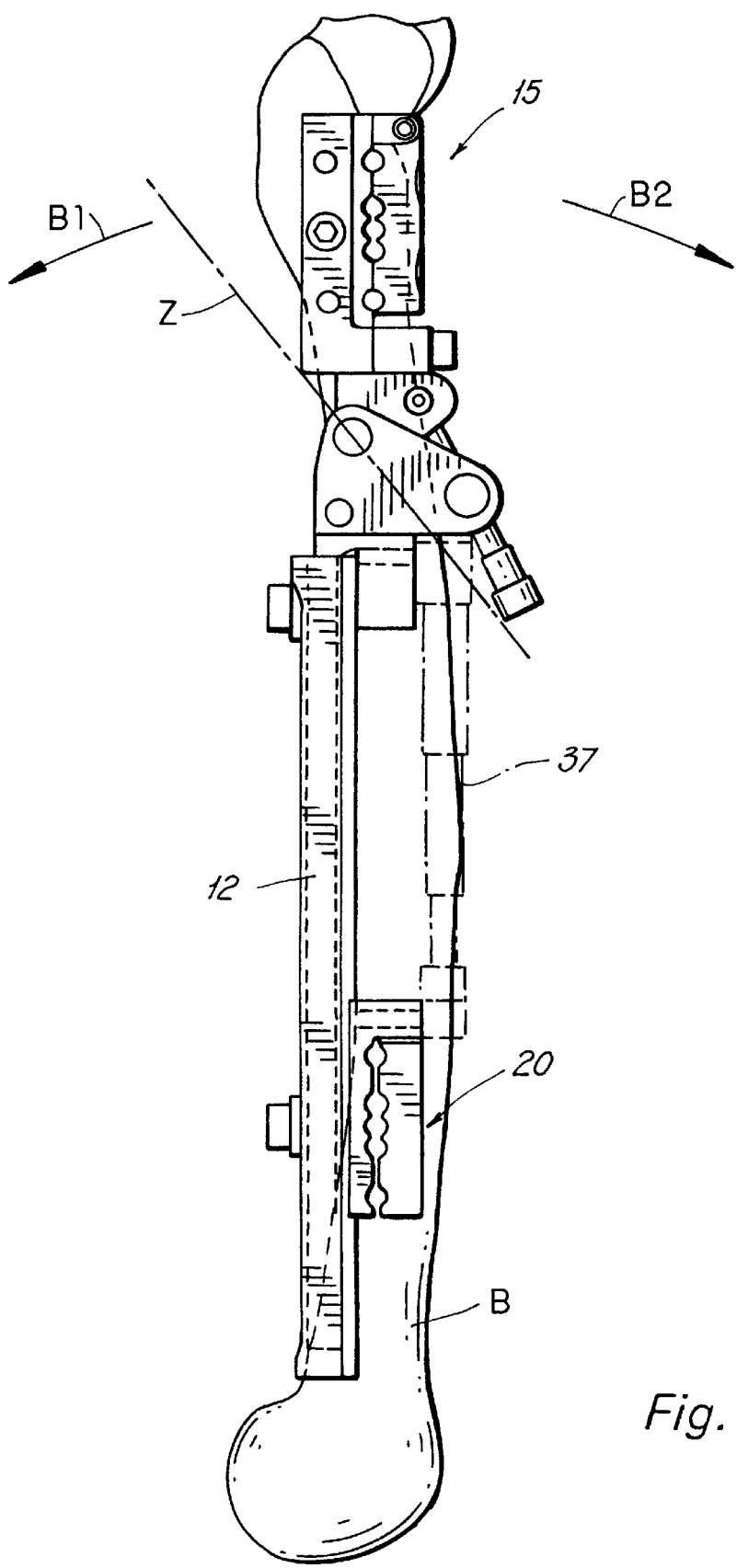
FIG. 2 is a side elevational view of the invention of FIG. 1 with jack assembly being rotated 90 degrees in the counterclockwise direction, as viewed from above, relative to proximal bone screw clamp and proximal anchor to enable correction of a bone deformity in the front-rear plane illustrated by arrows B1, B2.

Advantageously, bracket and tray locking screws 60a, 110a are provided for securely locking against rotation about the respective axes X and Z, to thereby define a predetermined geometric plane for angular correction, in the lateral directions indicated by arrows A1, A2 in FIG. 1. Orthopaedic device 10 of FIG. 1 is shown in FIG. 2, for active bone-defect correction in the front-back direction indicated by arrows B1, B2, in FIG. 2, about axis Y, by rotating control end 90a of differential screw assembly 80a.

Drill guides clamped in cantilevered clamp assembly 250, shown in FIGS. 13 to 14, may be translated relative to guide rail 12 parallel to the longitudinal axis R of guide rail 12 by virtue of the coupling between distal tenon 260 and the guide rail, described hereinabove. Additionally, drill guides clamped in cantilevered clamp assembly 250 may be pivoted in a plane parallel to support face 258 by rotating cover 268 about the central axis of the shaft of clamp locking screw 270, described hereinabove.

Orthopaedic device 10, when clamped to proximal and distal bone screws 17, 22 anchored in a deformed bone B, may be used to reposition the bone to a correct shape. For example, proximal bone screw clamp 170 may be disassembled from upper jack bracket 65a by removing tray locking screw 110a from tray socket 100a so that bracket boss 75a no longer obstructs separation of tray foot 97a from the upper jack bracket. Tray foot 97, with tray locking screw 110 removed therefrom, may then be placed on upper jack bracket 65 such that bracket boss 75 is received in tray socket 100. Tray locking screw 110 may then be inserted into tray foot 97 and thereby into tray socket 100 to obstruct separation of tray foot 97 from upper jack bracket 65.

Proximal bone screw clamp 117, shown in FIGS. 1 to 4, may be pivoted about axes X, Y, Z in the manner described hereinabove for proximal bone screw clamp 170. Additionally, proximal bone screw clamp 117 may be translated relative to tray base 95 by rotation of micrometric adjustment screw 120, described hereinabove. Micrometric adjustment screw 120, and differential screw assembly 80 enable small adjustments in the positions of proximal bone screws 17 enabling gradual correction of the shape of bone B.

Bone screws 17, 22 clamped between first and second jaws 187, 197 of swivel clamp assembly 184, shown in FIGS. 7 to 9, may be translated relative to guide rail 12 parallel to guide rail axis R by virtue of the coupling between dovetail tenon 204 and the guide rail, described hereinabove. Such relative translation imparts axial tension or compression to bone B thereby to tend to change the length of the bone between the connections thereof to swivel clamp assembly 184 and the adjacent clamp assembly. Additionally, first and second jaws 187, 197 may be swivelled relative to support plate 185 about axis 189, and locked in selected angles by locking screw 190. Swivel clamp assembly 210 provides similar positioning of bone screws 17, 22 as swivel clamp assembly 184, but has a different structure for coupling to guide rail 12, described hereinabove.

Swivel clamp assemblies 184, 210 may be positioned in a medial position of guide rail 12, for example between proximal clamp assembly 15 and a distal clamp assembly 20 of a standard type. So locating swivel clamp assemblies 184, 210 may enable clamping of the respective swivel clamp assembly to bone screws in the medial portion of a bone B which is bowed such that the medial portion is laterally displaced from guide rail 12.

Distal bone screws 22 clamped in oscillating clamp assembly 285, shown in FIGS. 16 to 20, may be translated relative to guide rail 12 parallel to guide rail axis R by virtue of the coupling between screw 291 and the guide rail, and in some embodiments a tenon and the guide rail, described hereinabove. Such relative translation imparts axial tension or compression to bone B thereby to tend to change the length of the bone between the connections thereof to oscillating clamp assembly 285 and proximal clamp assembly 15. Additionally, distal bone screws 22 clamped in oscillating clamp assembly 285 may be pivoted in a plane parallel to base seat 293 by rotating cover 296 about axis S, described hereinabove. Screw 311 enables small adjustments in the positions of distal bone screws 22 enabling gradual correction of a misshaped bone B in the plane C1–C2 shown in FIG. 16.

When manipulating proximal and distal clamp assemblies 15, 20 about a particular axis, it may be desirable to fix the respective clamp assemblies 15, 20 about the other axes and directions of manipulation, described hereinabove. Before manipulation of bone B, sections thereof transverse to the central axis thereof may be removed to facilitate the manipulation.

What is claimed is:

1. Orthopaedic device for the gradual correction of angular and longitudinal defects of elongated bones, comprising at least one first clamp for a first group of screws insertable in a proximal portion of a bone, and at least one second clamp for a second group of screws insertable in a distal portion of the bone, a longitudinal guide bar positioned externally of the limb to be corrected for slidably supporting said clamps in longitudinally distanced positions, at least one of said clamps being selectively angularly orientable relative to said other clamp about a substantially transverse axis for carrying out angular corrections of the bone, said orthopaedic device further comprising compression/distraction means movably connected to said first and second clamps for carrying out longitudinal corrections of the bone, said at least one orientable clamp having angular adjustment means for changing the relative angular positions of said clamps in a predetermined geometric plane, as well as transverse adjustment means coupleable with the group of bone screws carried by said clamp for repositioning the clamp along the length of the screws to compensate for the lateral or longitudinal movement of the clamp relative to the bone induced by the angular correction.

2. Orthopaedic device according to claim 1, wherein said at least one orientable clamp has axial orientation means for selectively defining said angular adjustable geometric plane.

3. Orthopaedic device according to claim 1, wherein said at least one orientable clamp comprises an attachment portion movably anchorable to said longitudinal bar upon which there is mounted a bracket pivotal about a substantially longitudinal first axis.

4. orthopaedic device according to claim 1, wherein the other one of said clamps is of the oscillating type and has a base anchorable to said bar with a substantially flat external surface.

5. Orthopaedic device for the gradual correction of angular and longitudinal defects of elongated bones, comprising at least one first clamp for a first group of screws insertable in a proximal portion of a bone, and at least one second clamp for a second group of screws insertable in a distal portion of the bone, a longitudinal guide bar positioned externally of the limb to be corrected for slidably supporting said clamps in longitudinally distanced positions, at least one of said clamps being selectively angularly orientable relative to said other clamp about a substantially transverse axis for carrying out angular corrections of the bone, said orthopaedic device further comprising compression/distraction means movably coupleable with at least one of said clamps for carrying out longitudinal corrections of the bone, said at least one orientable clamp having angular adjustment means for changing the relative angular positions of said clamps in a predetermined geometric plane, as well as transverse adjustment means coupleable with the group of bone screws carried by said clamp for repositioning the clamp along the length of the screws to compensate for the lateral or longitudinal movement of the clamp relative to the bone induced by the angular correction, wherein said angular and transverse adjustment means are of a micrometric type.

6. Orthopaedic device for the gradual correction of angular and longitudinal defects of elongated bones, comprising at least one first clamp for a first group of screws insertable in a proximal portion of a bone, and at least one second clamp for a second group of screws insertable in a distal portion of the bone, a longitudinal guide bar positioned externally of the limb to be corrected for slidably supporting said clamps in longitudinally distanced positions, at least one of said clamps being selectively angularly orientable relative to said other clamp about a substantially transverse axis for carrying out angular corrections of the bone, said orthopaedic device further comprising compression/distraction means movably coupleable with at least one of said clamps for carrying out longitudinal corrections of the bone, said at least one orientable clamp having angular adjustment means for changing the relative angular positions of said clamps in a predetermined geometric plane, as well as transverse adjustment means coupleable with the group of bone screws carried by said clamp for repositioning the clamp along the length of the screws to compensate for the lateral or longitudinal movement of the clamp relative to the bone induced by the angular correction, wherein said at least one orientable clamp comprises an attachment portion movably anchorable to said longitudinal bar upon which there is mounted a bracket pivotal about a substantially longitudinal first axis, wherein on said bracket there is hinged about a substantially transverse axis an intermediate body united to said bracket by means of a screw and female thread micrometric adjusting mechanism.

7. Orthopaedic device according to claim 6, wherein on said intermediate body there is mounted a substantially L-shaped support rotatable about a substantially longitudinal second axis.

8. Orthopaedic device according to claim 7, wherein said support has transverse guiding means for a jaw of said clamp and a screw and female thread micrometric adjustment mechanism for promoting the controlled translation of said jaw along said transverse guiding means.

9. Orthopaedic device according to claim 7, wherein there are provided stop means for each of said substantially longitudinal rotation axes for selectively determining the angular adjustment plane of the clamp.

10. Orthopaedic device for the gradual correction of angular and longitudinal defects of elongated bones, comprising at least one first clamp for a first group of screws insertable in a proximal portion of a bone, and at least one second clamp for a second group of screws insertable in a distal portion of the bone, a longitudinal guide bar positioned externally of the limb to be corrected for slidably supporting said clamps in longitudinally distanced positions, at least one of said clamps being selectively angularly orientable relative to said other clamp about a substantially transverse axis for carrying out angular corrections of the bone, said orthopaedic device further comprising compression/distraction means movably coupleable with at least one of said clamps for carrying out longitudinal corrections of the bone, said at least one orientable clamp having angular adjustment means for changing the relative angular positions of said clamps in a predetermined geometric plane, as well as transverse adjustment means coupleable with the group of bone screws carried by said clamp for repositioning the clamp along the length of the screws to compensate for the lateral or longitudinal movement of the clamp relative to the bone induced by the angular correction, wherein the other one of said clamps is of the oscillating type and has a base anchorable to said bar with a substantially flat external surface, wherein on said base there is mounted a cover oscillatable about an axis substantially perpendicular to the longitudinal axis of said bar.

11. orthopaedic device according to claim 10, wherein there are provided screw and female thread adjustment means adapted to selectively control the angular position of said cover with respect to said base, with said screw provided with holding means towards both its longitudinal ends.

12. Orthopaedic device according to claim 10, wherein there is provided a cuneiform stop screwable to said base for selectively engaging on the bottom of a circular seat with a bottom substantially countershaped with respect to the stop formed on the external face of said cover.

13. Orthopaedic device according to claim 10, wherein said cover has an internal face which faces said base, the internal face of said cover having a plurality of transverse seats for the bone screws, said transverse seats having transverse sections of greater size than the maximum diameter of the screws and a V-shaped bottom for allowing the screws to slide parallel to themselves in case of loosening of the cover.

14. Orthopaedic device according to claim 1, wherein there is provided a further clamp for locking a group of screws insertable in medial and distal portions of the bone.

15. Orthopaedic device for the gradual correction of angular and longitudinal defects of elongated bones, comprising at least one first clamp for a first group of screws insertable in a proximal portion of a bone, and at least one second clamp for a second group of screws insertable in a distal portion of the bone, a longitudinal guide bar positioned externally of the limb to be corrected for slidably supporting said clamps in longitudinally distanced positions, at least one of said clamps being selectively angularly orientable relative to said other clamp about a substantially transverse axis for carrying out angular corrections of the bone, said orthopaedic device further comprising compression/distraction means movably coupleable with at least one of said clamps for carrying out longitudinal corrections of the bone, said at least one orientable clamp having angular adjustment means for chancing the relative angular positions of said clamps in a predetermined geometric plane, as well as transverse adjustment means coupleable with the group of bone screws carried by said clamp for repositioning the clamp along the length of the screws to compensate for the lateral or longitudinal movement of the clamp relative to the bone induced by the angular correction, wherein there is provided a further clamp for locking a group of screws insertable in medial and distal portions of the bone, wherein said medial clamp is of the basculant type, and is formed by a support plate anchorable to said bar to which is hinged with a substantially longitudinal axis a first jaw of said clamp to which is coupleable a second jaw by means of locking screws.

16. Orthopaedic device according to claim 15, wherein said support plate has means for connecting to said bar constituted by a dovetail tenon engageable, before the mounting of the other clamps, in a countershaped seat formed along said bar and by a stop screw passing through a longitudinal groove of said bar.

17. Orthopaedic device according to claim 15, wherein said support plate has means for connecting to said bar constituted by a connection block screwed to said plate for blocking the separation of the bar also after the mounting of the other clamps.

18. A fixator for use in correcting a bone deformity comprising:

an elongate guide rail having a longitudinal axis and at least one elongate generally flattened face; and first and second clamp assemblies each having respective first and second anchor elements at least one of which is adjustably positionable in one of said respective proximal and distal regions of said guide rail on said face thereof, said first and second anchor elements being keyed to said guide rail face to fix said first and second clamps thereto and to limit said adjustable positioning to translation in the direction of said guide rail axis, said first and second clamp assemblies having respective first and second bone screw clamps, said first clamp assembly having a pivot joint for connecting said first bone screw clamp to said first anchor element, said pivot joint defining a lateral pivot axis transverse to said rail axis, said first clamp assembly having means for locking said first bone screw clamp at selected angles about said lateral pivot axis relative to said rail axis, said translation of said first bone screw clamp between said selected angles defining a pivot plane, said pivot joint further defining an annular pivot axis pivotal about said lateral pivot axis between parallel and inclined orientations relative to said rail axis by said angle of pivot of said first bone screw clamp, said locking means further locking said first bone screw clamp at selected angles about said angular pivot axis relative to said pivot plane, said pivot joint further defining a longitudinal pivot axis parallel to said rail axis, said locking means further locking said pivot joint at selected angles about said longitudinal pivot axis relative to said pivot plane, said second clamp assembly including means for locking said second bone screw clamp to said second anchor element.

19. A fixator for use in correcting a bone deformity comprising:

an elongate guide rail having a longitudinal axis and at least one elongate generally flattened face; and first and second clamp assemblies each having respective first and second anchor elements at least one of which is adjustably positionable in one of said respective proximal and distal regions of said guide rail on said face thereof, said first and second anchor elements being keyed to said guide rail face to fix said first and second clamps thereto and to limit said adjustable positioning to translation in the direction of said guide rail axis, said first and second clamp assemblies having respective first and second bone screw clamps, said first clamp assembly having a pivot joint for connecting said first bone screw clamp to said first anchor element, said pivot joint defining a first pivot axis transverse to said rail axis, said first clamp assembly having means for locking said first bone screw clamp at selected angles about said pivot axis relative to said rail axis, said translation of said first bone screw clamp between said selected angles defining a pivot plane, said pivot point further defining a second pivot axis inclined from said rail axis by said angle of pivot of said first bone screw clamp, said locking means further locking said first bone screw clamp at selected angles about said second pivot axis relative to said pivot plane, said pivot joint further defining a third pivot axis parallel to said rail axis, said locking means further locking said pivot joint at selected angles about said third pivot axis relative to said pivot plane, said second clamp assembly including means for locking said second bone screw clamp to said second anchor element, wherein said second clamp assembly includes a swivel clamp and means for locking said swivel clamp at preselected angles about an axis parallel to and offset from said guide rail axis.

20. A fixator for use in correcting a bone deformity comprising:

an elongate guide rail having a longitudinal axis and at least one elongate generally flattened face; and first and second clamp assemblies having respective first and second anchor elements adjustably positionable in respective proximal and distal regions of said guide rail on said face thereof, said first and second anchor elements being keyed to said guide rail face to fix said first and second clamps thereto and to limit said adjustable positioning to translation in the direction of said guide rail axis, said first and second clamp assemblies having respective first and second bone screw clamps, said first clamp assembly having a pivot joint for connecting said first bone screw clamp to said first anchor element, said pivot joint defining a pivot axis transverse to said rail axis, said pivot joint enabling said first bone screw clamp to pivot about said pivot axis relative to said rail axis, said first clamp assembly including a screw one end of which is rotatably mounted on one of said second anchor element and bone screw clamp, said first clamp assembly further including a threaded sleeve mounted on the other of said second anchor element and bone screw clamp, said screw being threaded through said sleeve for rotation in opposed directions therein such that said opposite rotation of said screw to oscillatingly pivot said second bone screw clamp relative to said second anchor element about said pivot axis, said first clamp assembly further having means for locking said first bone screw clamp at selected angles about said pivot axis relative to said rail axis, said second clamp assembly including means for locking said second bone screw clamp to said second anchor element.

21. A fixator as set forth in claim 20, wherein said second clamp assembly includes a swivel clamp and means for locking said swivel clamp at preselected angles about an axis parallel to and offset from said guide rail axis.

22. A fixator as set forth in claim 20, and further comprising a reversible bracket for coupling said screw to one of said second anchor element and bone screw clamp to provide right- and left-hand operation of said screw.

23. A fixator for use in correcting a bone deformity comprising:

an elongate guide rail having a longitudinal axis and at least one elongate generally flattened face; and first and second clamp assemblies each having respective first and second anchor elements at least one of which is adjustably positionable in one of said respective proximal and distal regions of said guide rail on said face thereof, said first and second anchor elements being keyed to said guide rail face to fix said first and second clamps thereto and to limit said adjustable positioning to translation in the direction of said guide rail axis, said first and second clamp assemblies having respective first and second bone screw clamps, said first clamp assembly having a pivot joint for connecting said first bone screw clamp to said first anchor element, said pivot joint defining a lateral pivot axis transverse to said rail axis, said first clamp assembly having means for locking said first bone screw clamp at selected angles about said lateral pivot axis relative to said rail axis, said translation of said first bone screw clamp between said selected angles defining a pivot plane, said pivot joint further defining an angular pivot axis inclined from said rail axis by said angle of pivot of said first bone screw clamp, said locking means further locking said first bone screw clamp at selected angles about said angular pivot axis relative to said pivot plane, said pivot joint further defining a longitudinal pivot axis parallel to said rail axis, said locking means further locking said pivot joint at selected angles about said longitudinal pivot axis relative to said pivot plane, said second clamp assembly including means for locking said second bone screw clamp to said second anchor element, said second clamp assembly including a swivel clamp and means for locking said swivel clamp at preselected angles about an axis transverse to and offset from said guide rail axis.

24. A fixator as set forth in claim 20, wherein said second clamp assembly includes a swivel clamp and means for locking said swivel clamp at preselected angles about an axis transverse to and offset from said guide rail axis.

* * * * *